(12) United States Patent
Chun et al.

(10) Patent No.: US 11,458,310 B2
(45) Date of Patent: Oct. 4, 2022

(54) ELECTRO-STIMULATION TYPE INDOOR BICYCLE

(71) Applicant: Y & J BIO CO., LTD., Seoul (KR)

(72) Inventors: Young Sam Chun, Goyang-si (KR); Hyoung Tae Kim, Goyang-si Gyeonggi-do (KR)

(73) Assignee: Y & J BIO CO., LTD., Seoul (KR)

( * ) Notice: Subject to any disclaimer, the term of this patent is extended or adjusted under 35 U.S.C. 154(b) by 263 days.

(21) Appl. No.: 16/650,175

(22) PCT Filed: Sep. 21, 2018

(86) PCT No.: PCT/KR2018/011294
§ 371 (c)(1),
(2) Date: Mar. 24, 2020

(87) PCT Pub. No.: WO2019/066426
PCT Pub. Date: Apr. 4, 2019

(65) Prior Publication Data
US 2020/0230405 A1 Jul. 23, 2020

(30) Foreign Application Priority Data
Sep. 26, 2017 (KR) .................. 10-2017-0124339

(51) Int. Cl.
*A61N 1/36* (2006.01)
*A61N 1/04* (2006.01)
(Continued)

(52) U.S. Cl.
CPC ....... *A61N 1/36003* (2013.01); *A61N 1/0452* (2013.01); *A61N 1/0492* (2013.01);
(Continued)

(58) Field of Classification Search
None
See application file for complete search history.

(56) References Cited

U.S. PATENT DOCUMENTS 4,499,900 A * 2/1985 Petrofsky ............. A61H 1/0214
607/48
4,809,696 A * 3/1989 Laenger ............. A61N 1/36003
607/48
(Continued)

FOREIGN PATENT DOCUMENTS

JP 07-037642 Y2 8/1995
JP 2000126331 A * 5/2000 ........... A61B 5/4872
(Continued)

*Primary Examiner* — Sundhara M Ganesan
*Assistant Examiner* — Shila Jalalzadeh Abyaneh
(74) *Attorney, Agent, or Firm* — Novick, Kim & Lee, PLLC; Jae Youn Kim; Jihun Kim

(57) ABSTRACT

An electrical stimulation indoor bike includes a stationary bicycle; an electrical stimulation unit connected to the stationary bicycle either with wire or without wire, and including an electrode pad for applying electrical stimulation to a user's body; and a control unit to control electrical stimulation of the electrical stimulation unit in accordance with an exercise mode of the stationary bicycle. By the electrical stimulation indoor bike, a variety of electrical stimulation according to pedal movement is applied to a body through an indoor bike connected with a low-frequency stimulator, thereby maximizing exercise effect.

5 Claims, 6 Drawing Sheets

(51) Int. Cl.
*A63B 22/06* (2006.01)
*A63B 24/00* (2006.01)

(52) U.S. Cl.
CPC ......... *A61N 1/3603* (2017.08); *A63B 22/0605* (2013.01); *A63B 24/0087* (2013.01); *A63B 2213/004* (2013.01); *A63B 2220/30* (2013.01)

(56) References Cited

U.S. PATENT DOCUMENTS

| | | | | |
|---|---|---|---|---|
| 4,863,157 | A * | 9/1989 | Mendel | A61N 1/36003 280/282 |
| 4,947,836 | A * | 8/1990 | Laenger | A61N 1/36003 482/57 |
| 5,230,673 | A | 7/1993 | Maeyama et al. | |
| 5,294,786 | A | 3/1994 | Maeyama et al. | |
| 5,702,323 | A * | 12/1997 | Poulton | A63B 24/00 482/8 |
| 8,249,714 | B1 * | 8/2012 | Hartman | A63B 23/03525 607/48 |
| 8,992,384 | B2 * | 3/2015 | Hamada | A61N 1/36014 482/901 |
| 10,173,058 | B2 * | 1/2019 | Duncan | A61B 5/11 |
| 2004/0023759 | A1 * | 2/2004 | Duncan | A61N 1/36003 482/57 |
| 2005/0015118 | A1 * | 1/2005 | Davis | A61H 1/02 607/49 |
| 2006/0247095 | A1 * | 11/2006 | Rummerfield | A61H 1/0214 482/57 |
| 2007/0208392 | A1 * | 9/2007 | Kuschner | A61N 1/36003 607/48 |
| 2013/0053734 | A1 * | 2/2013 | Barriskill | A61H 1/0229 601/5 |
| 2013/0065730 | A1 * | 3/2013 | Camerota | A63B 24/0062 482/5 |
| 2017/0100586 | A1 * | 4/2017 | Akiba | A61B 5/224 |
| 2018/0036531 | A1 * | 2/2018 | Schwarz | G16H 20/30 |
| 2018/0056061 | A1 * | 3/2018 | Nishimura | A63B 22/0605 |

FOREIGN PATENT DOCUMENTS

| | | | |
|---|---|---|---|
| JP | 2003-117006 | A | 4/2003 |
| JP | 2003117006 | A * | 4/2003 |
| JP | 2003144556 | A * | 5/2003 |
| JP | 2004-504921 | A | 2/2004 |
| KR | 20-0447430 | Y1 | 1/2010 |
| KR | 10-1392065 | B1 | 5/2014 |
| WO | 02-13694 | A1 | 2/2002 |

* cited by examiner

ELECTRO-STIMULATION TYPE INDOOR BICYCLE

TECHNICAL FIELD

The present invention relates to an electrical stimulation indoor bike, and more particularly, to an indoor bike combined with a low frequency stimulator.

BACKGROUND ART

An exercise method of using a low frequency stimulator is a method of using a phenomenon in that muscles contract when electrical stimulation is applied to the body, that is, a method of contacting an electrode pad which generates a low frequency to a user's body and then applying a weak electrical stimulation to the electrode pad contacted to the body during exercise.

This exercise method has been spotlighted by modern people for the reason that it can provide the effect of long-time exercise even only with short time exercise.

The user improves the effect for weight loss and muscle training by wearing a low frequency stimulator device such as a portable stimulator detachable to the body and an EMS training suit worn all over the body and performing various exercises that the user wants.

On the other hand, the most widely used exercise equipment for an aerobic exercise are a treadmill, an indoor bike, etc.

So far, there hasn't been proposed any exercise device in which an aerobic exercise equipment is combined with a low frequency stimulator, and if a function of the low frequency stimulator is combined with an intrinsic function of a treadmill and an indoor bike, the exercise effect is expected to be maximized.

Accordingly, the present inventors have proposed an optimal exercise program and a device combining the intrinsic exercise function of an indoor bike with the function of a low frequency stimulator.

DETAILED DESCRIPTION OF THE INVENTION

Technical Problem

The present invention can further maximize the effect of weight loss and exercise by adding the effect of low-frequency stimulation to that of an intrinsic aerobic exercise program of an indoor bike. In addition, it can compensate for a disadvantage that a traditional indoor bike has no auxiliary means for maintaining the speed of the bike depending on the automatic speed profile unlike the treadmill, and can assist a user to maintain the speed profile program provided therein.

Technical Solution

The above object can be achieved by an electrical stimulation indoor bike according to an aspect of the present invention, characterized by comprising: a stationary bicycle; an electrical stimulation unit connected to the stationary bicycle either with wire or without wire, and including an electrode pad for applying electrical stimulation to a user's body; and a control unit to control electrical stimulation of the electrical stimulation unit in accordance with an exercise mode of the stationary bicycle.

Here, the electrical stimulation indoor bike can be characterized in that when a pedal load of the stationary bicycle is input by a user or predetermined, the control unit provides a basic stimulation level corresponding to the pedal load, and controls electrical stimulation of the electrical stimulation unit so as to generate stronger stimulation than the basic stimulation level in proportion to a rotation speed of a pedal.

In addition, the electrical stimulation indoor bike can be characterized in that the exercise mode includes a plurality of programs that define a pedal load or a speed profile of the stationary bicycle selected by a user's input, and the control unit changes an intensity or a frequency of electrical stimulation generated at the electrical stimulation unit in accordance with the pedal load or the speed profile.

And the electrical stimulation indoor bike can be characterized in that the control unit controls the electrical stimulation unit so as to generate stronger electrical stimulation than electrical stimulation corresponding to the speed profile, when a rotation speed of the pedal is slower than that of being defined in the speed profile.

Here, the electrical stimulation indoor bike can be characterized in that an intensity of electrical stimulation corresponding to the speed profile changes depending on the pedal load, when the pedal load and one of the plurality of programs are selected together.

In addition, the electrical stimulation indoor bike can be characterized in that the electrical stimulation unit includes a plurality of electrode pads, and the control unit controls electrical stimulation of the electrical stimulation unit so that a current selectively flows to each electrode pad of the plurality of electrode pads.

And the electrical stimulation indoor bike can be characterized in that the control unit controls electrical stimulation of the electrical stimulation unit so that a current can flow to an electrode pad attached to a user's upper body muscles which respond in accordance with the lowering of the pedal when a user lowers the pedal of the stationary bicycle.

Here, the electrical stimulation indoor bike can be characterized in that the speed profile comprises a warm-up step in which the pedal starts rotating and increases a rotation speed up to a predetermined speed at low speed, an intensive exercise step in which the pedal rotates starting from the predetermined speed to a higher speed, and a finishing step in which the pedal rotates from the speed of the intensive exercise step to the speed of being stopped at a low speed, wherein the control unit controls the electrical stimulation unit so as to generate electrical stimulation corresponding to each step.

In addition, the electrical stimulation indoor bike can be characterized in that the electrical stimulation unit includes a heat providing unit for providing heat to a user's body area attached by electrode pad, and the heat providing unit relaxes muscles of the body to which the electrode pad is attached at the warm-up step.

Advantageous Effects

According to the present invention, since various electrical stimulations are applied to the body through the indoor bike combined with the low frequency stimulator, the exercise effect is maximized. In addition, since electrical stimulation is applied for a user to perform exercise according to the speed profile of the program embedded in the indoor bike, the user may be assisted to maintain the pedal speed steadily according to the provided exercise program.

BEST MODE

Hereinafter, embodiments of the present invention will be described with reference to the accompanying drawings in detail; However, detailed descriptions of well-known functions or configurations that may obscure the subject matter of the present invention will be omitted for simplicity and clarity of description.

Figure 1:
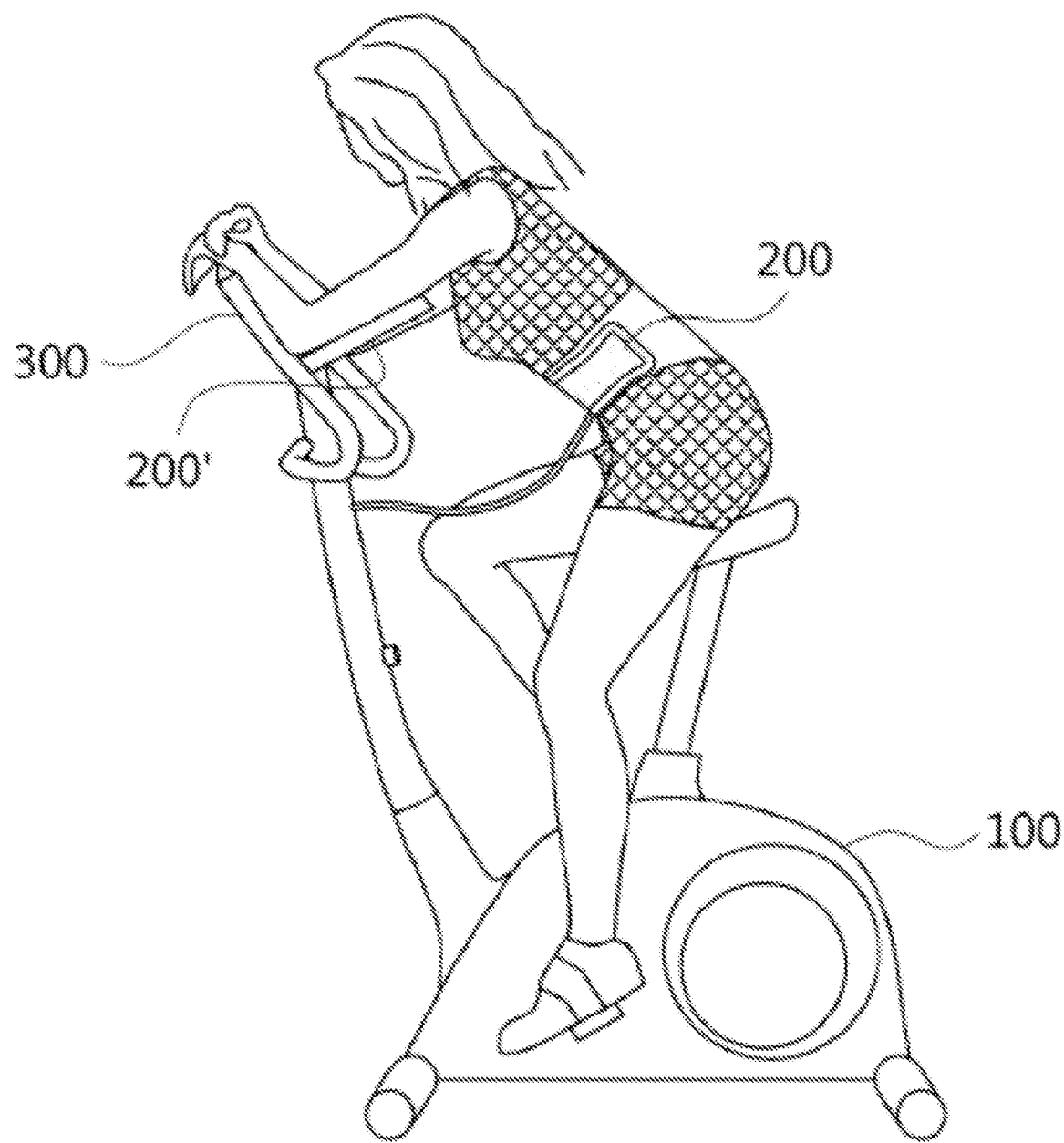
FIGS. 1 to 3 are schematic views of an electrical stimulation indoor bike according to embodiments of the present invention.
Figure 2:
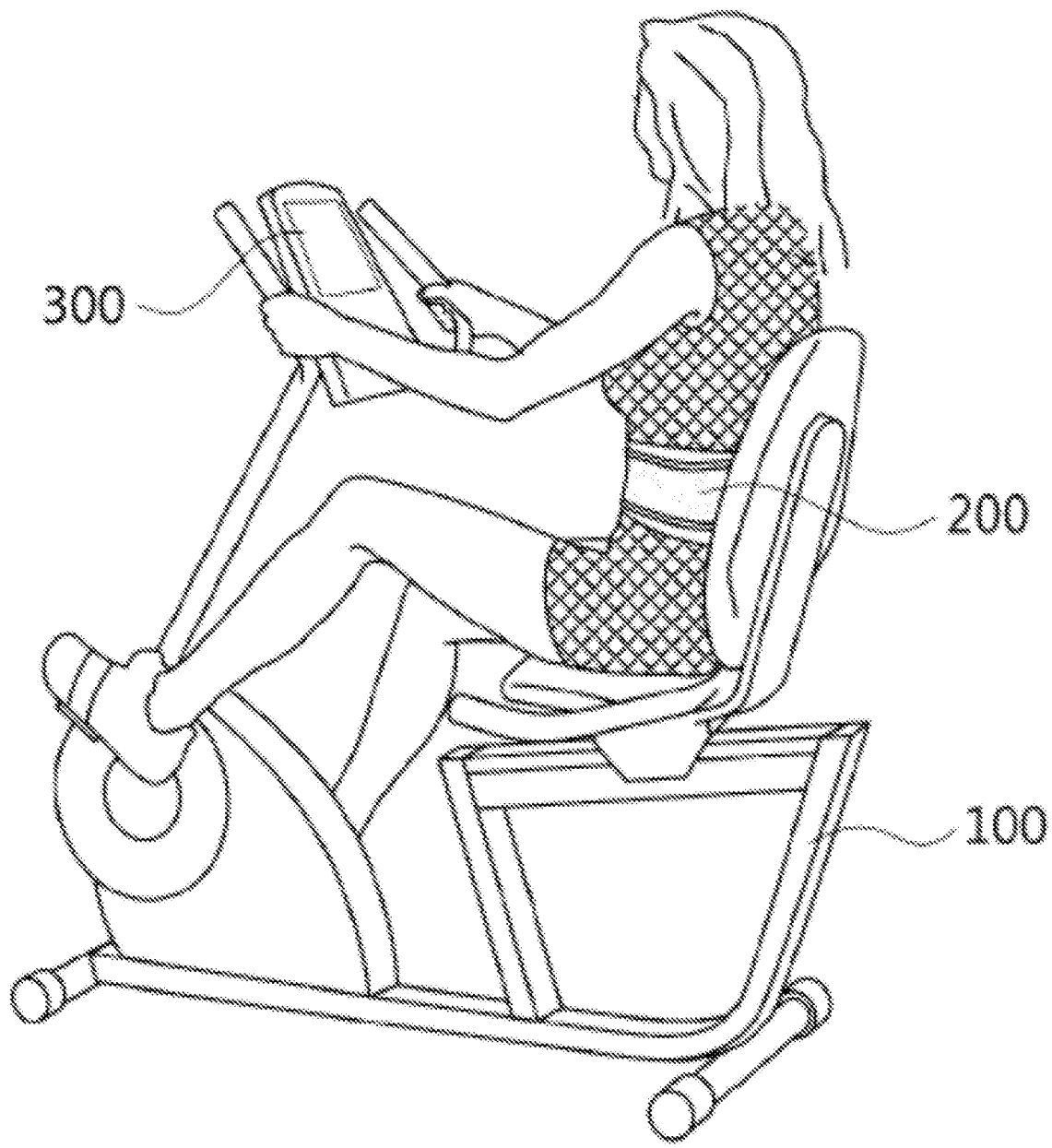
Figure 3:
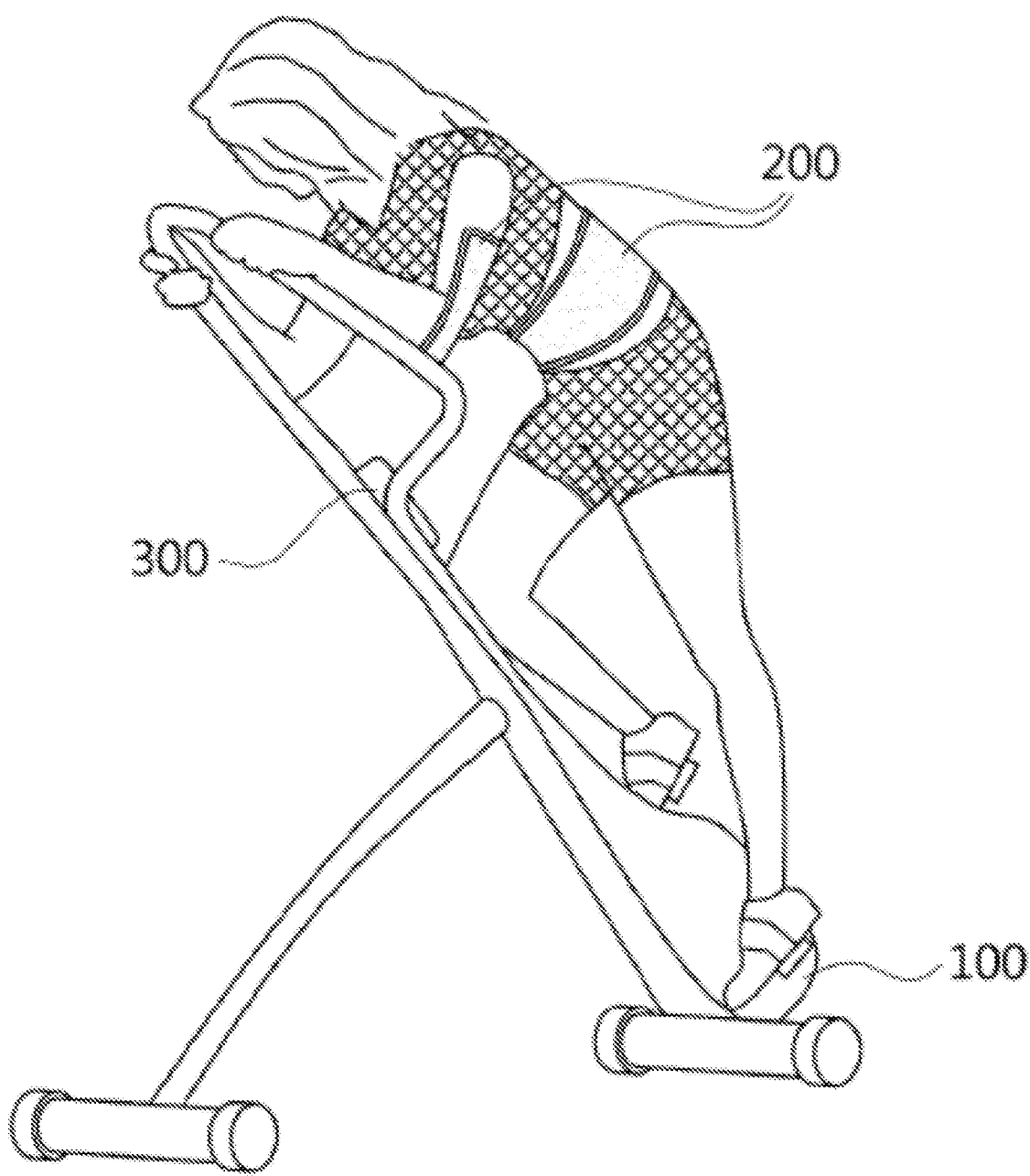

FIGS. 1, 2 and 3 show the outline of the electrical stimulation indoor bike according to the embodiment of the present invention.

Referring to FIGS. 1 to 3, the electrical stimulation indoor bike according to an embodiment of the present invention includes a stationary bicycle 100, an electrical stimulation unit 200, a user input unit (not shown), and a control unit 300.

The stationary bicycle 100 is an indoor fitness bicycle used for a user to exercise indoors, and is composed of a body, a saddle, a pedal and a cradle. FIGS. 1 to 3 schematically show indoor fitness bicycles that can be variously implemented, FIG. 1 shows a folding fitness bicycle, FIG. 2 shows a seated fitness bicycle, and FIG. 3 shows a standing fitness bicycle.

The stationary bicycle 100 may include a charging unit (not shown) for storing the power energy generated by a user's pedal rotational movement as electrical energy, and the electricity stored by the charging unit (not shown) may be connected, through a USB port, etc., to a product requiring current supply such as a personal portable terminal, which can be located in the front frame of the fitness bike.

The electrical stimulation unit 200 is connected to the stationary bicycle 100 either with wire or without wire, and is associated to pedal exercise of the stationary bicycle 100.

The electrical stimulation unit 200 may be fixed to a frame of the stationary bicycle 100 or may be connected to the stationary bicycle 100 through a connecting terminal of the electrical stimulation unit 200. Specifically, referring to the connecting method between the electrical stimulation unit 200 and the stationary bicycle 100, as shown in FIG. 1, the electrical stimulation unit 200 is connected to the front frame of the stationary bicycle 100 with wire, and a user may use it by wearing it on an abdomen. In addition, the electrical stimulation unit 200' may be fixed to be connected to a handle portion on which a user's arm can be leaned, and electrical stimulation according to the movement of the stationary bicycle 100 may be implemented to be applied to the arm.

In addition, the electrical stimulation unit 200 may be connected to the stationary bicycle 100 wirelessly. For example, a user may attach a communication module to the electrical stimulation unit 200 and connect the communication module to the stationary bicycle 100 by using various communication methods including ZIGBEE, BLUETOOTH, etc. Here, the communication module may be implemented as a communication chip, and the communication chip refers to a chip which performs communication according to various wireless communication standards such as WiFi, Bluetooth, Zigbee, etc.

Here, the electrical stimulation unit 200 may be implemented as a low frequency muscle stimulator, and may be used independently from the stationary bicycle 100. A user may use the electrical stimulation unit 200 by independently adjusting electrical stimulation through an input unit of the electrical stimulation unit 200.

The electrical stimulation unit 200 may be provided in a form where it can be freely detachable by attaching it to a user's arm or abdomen or wrapping a user's arm or abdomen with it, such as a wristband or a belly band, and it may include a plurality of electrode pads for applying electrical stimulation to the contacted body area, and a plurality of heat providing units. On the other hand, although not shown in FIGS., the electrical stimulation unit 200 is implemented by further including a battery module for supplying electricity to the electrode pad, a wire for electrically connecting the battery module and the electrode pad.

At this time, the electrical stimulation unit 200 may be driven by a normal battery or by a battery that changes power energy generated by the pedal rotation of the stationary bicycle to electrical energy and store the electrical energy into.

The electrode pad of the electrical stimulation unit 200 is implemented in a form in which a plurality of electrode pads are connected to each other in order to be worn or be attached to an arm, a back, an abdomen, etc. of the user.

The plurality of electrode pads make electrical stimulation to be applied to the user's body by a current generated at the electrical stimulation unit 200. The method of applying the stimulation to the electrode pad may be variously implemented according to the order of the stimulation pad through which the current flows and the time during which the current flows.

Figure 4:
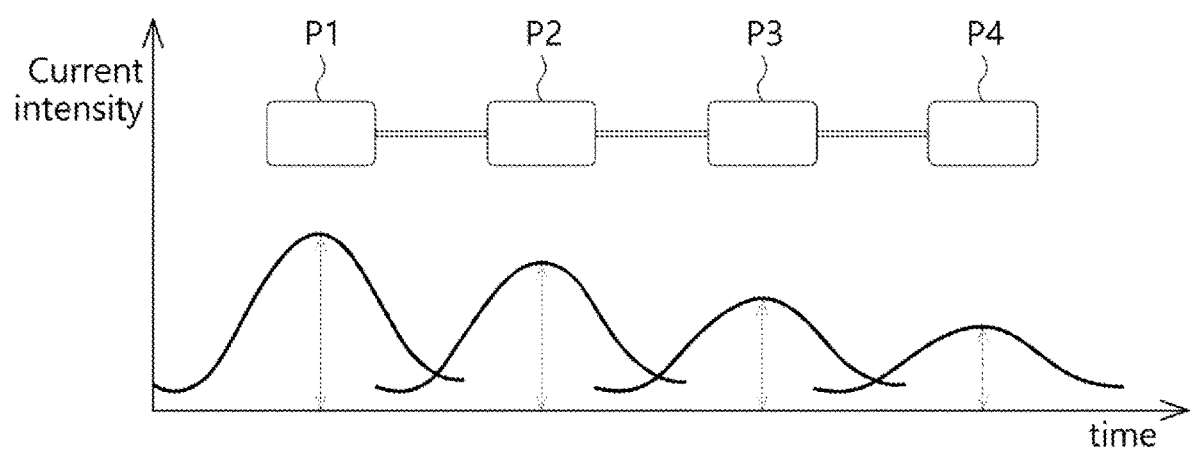
FIG. 4 is a graph showing a change in a current flowing through a plurality of electrode pads of an electrical stimulation unit according to an embodiment of the present invention.

FIG. 4 is a graph illustrating a change in a current flowing through a plurality of electrode pads of the electrical stimulation unit 200 according to an embodiment of the present invention.

In one embodiment, the electrical stimulation unit 200 may generate a current in P1, P2, P3, P4 at the same time and apply the stimulation to a user. In addition, the electrical stimulation unit 200 may maintain the same intensity of the current flowing through P1, P2, P3, and P4, or may vary the intensities of flowing current individually.

Referring to FIG. 4, the electrical stimulation unit 200 generates a current with a sequential intensity from P1 to P4 in consecutive electrode pads P1, P2, P3, and P4, and generates the strongest current in P1. The user who attaches the electrode pad shown in FIG. 2 may feel that stimulation proceeds sequentially in one direction, and may feel that intensity of the stimulation proceeding along the area attached with electrode pad is changed. Through a stepwise stimulation like this, the user may feel massage effect as if someone rubs on a topical area.

In addition, the electrical stimulation unit 200 includes not only an electrode pad but also a heat providing unit that provides heat to a local part of a user's body to which the electrode pad is attached. The heat providing unit may be implemented to include a heating wire. The heat providing unit functions in a warm-up step of a program speed profile in an exercise mode of the stationary bicycle 100 to be described later. Since the heat providing unit warms the area to which the electrode pad is attached, body temperature increases and muscles are relaxed to prevent the user from being injured, and the effect of alleviating a pain of the injured area can be obtained.

In a user input unit (not shown), an exercise mode of the stationary bicycle 100 is selected by a user. The exercise mode, here, includes a number of programs that define a pedal load or a speed profile of the stationary bicycle 100.

The user input unit may be implemented through a load control lever provided on the front pillar or frame of the stationary bicycle 100 to receive the pedal load, or may be implemented through a load control software of a program pre-stored in a memory (not shown). For example, the user may adjust the load to control the exercise intensity, which may vary the force of lower body part of the user for rotating the pedal depending on the selected load size.

In addition, the user input unit may be implemented through a touch display, a mode selection button, or the like installed on the front portion of the stationary bicycle 100. Here, when the user input unit is implemented as the touch display, a user may perform input by touching a GUI (Graphic User Interface) displayed on the display. In addition, the mode selection button may be implemented through a mechanical button, a wheel button, and the like, and the user may perform an input by operating a button such as pressing it or rotating it.

The stationary bicycle 100 may include a plurality of programs defining a speed profile including changes of a pedal load and a pedal rotation speed over time, so as to provide a user a change of exercise. Information about such a plurality of programs is stored in a memory (not shown). Accordingly, the user may select one of a plurality of programs through the user input unit and perform exercise.

The control unit 300 controls the electrical stimulation at the electrical stimulation unit 200 generated to the user to which the electrode pad is attached according to the exercise mode of the stationary bicycle 100, and changes an intensity or a frequency of electrical stimulation generated at the electrode pad according to the exercise mode.

When a user performs exercise using the pedal load selected by the user or the pre-set pedal load, the control unit 300 changes an intensity or a frequency of electrical stimulation generated at the electrical stimulation unit 200 according to the pedal load.

For example, a user may select out of the pedal loads provided from the 1st level to the 8th level on the stationary bicycle 100, and the pedal load is gradually increasing from the 1st to the 8th level.

When the user selects a load of the 2nd level, the electrical stimulation unit 200 generates an intensity or a frequency of electrical stimulation corresponding to the 2nd level of pedal load. When the user changes the load to the 6th level while preforming exercise, electrical stimulation corresponding to the load is applied to the user's body, and the control unit 300 controls the electrical stimulation unit 200 to generate stronger electrical stimulation than electrical stimulation of the $2^{nd}$ level. Electrical stimulation corresponding to each level of load may increase proportionally.

In addition, when a pedal load is set, the control unit 300 gives a basic stimulation level corresponding to the pedal load, and controls electrical stimulation so that stronger stimulation than the basic stimulation level is generated in proportion to a pedal rotation speed. Here, the basic stimulation level means the value of the lowest intensity and frequency of stimulation generated at the status of the pedal being stopped when a user wears an electrode pad and starts exercising.

As described above, the control unit 300 may in advance store reference information for controlling an intensity or a frequency of electrical stimulation to be provided to a user according to the pedal load, and may control the electrical stimulation unit 200 to provide electrical stimulation depending on the information stored according to the set pedal load. The control unit 300 may be implemented to include a memory for storing reference information for controlling, a microprocessor for generating a control command according to the reference information, and so on.

Figure 5:
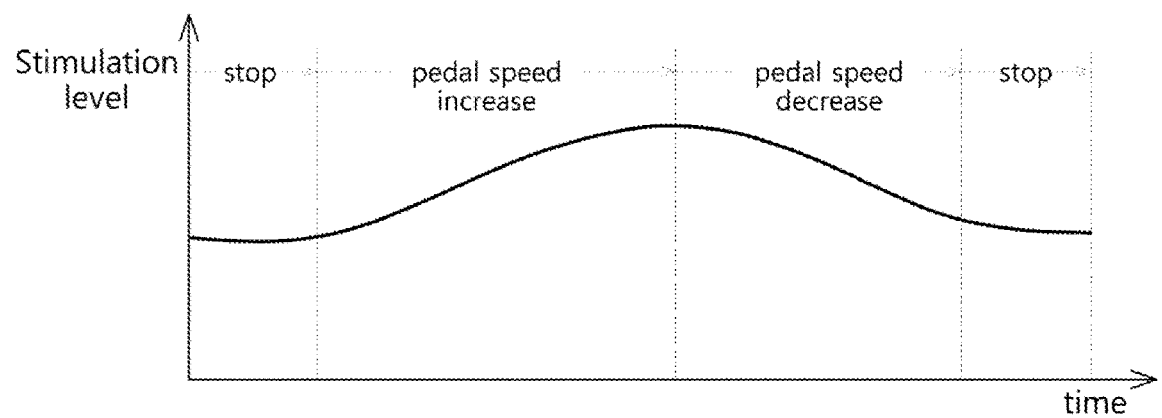
FIG. 5 is a graph showing an electrical stimulation level according to a change in pedal speed according to an embodiment of the present invention.

FIG. 5 is a graph illustrating electrical stimulation levels according to a change in pedal speed according to an embodiment of the present invention.

Specifically, FIG. 5 illustrates the electrical stimulation level when a user attaches an electrode pad to an abdomen and exercises with the electrical stimulation indoor bike according to an embodiment of the present invention.

Referring to the Y axis of the graph of FIG. 5, the stimulation level at the state of a pedal being stopped before starting exercising (when the time on the X axis is 0) represents the basic stimulation level. It can be assumed that a user is attached by an electrode pad and is on an indoor bike. The control unit 300 may provide a basic stimulation level corresponding to a pedal load preset before a pedal rotates, and recognize that such a stimulation is applied to a abdomen of a user. The control unit 300 may give an initial stimulation level suitable for a user in consideration of information such as a user's skin resistance value, a pedal load, a user's weight and height, etc., which are input at a preparation step.

Looking at the time of the X-axis of the graph, a pedal rotation speed increases over time, and the stimulation level gradually increases in proportion to increasing pedal rotation speed. As longer as a user performs exercise, the pedal rotation speed gradually increases, and the control unit 300 controls the electrical stimulation unit so as to increase a stimulation level by increasing an intensity or a frequency of electrical stimulation in proportion to the increasing pedal rotation speed.

Looking at a pedal speed increase section of the graph, when electrical stimulation occurs as a pedal rotation speed increases, stronger electrical stimulation is generated than the basic stimulation level. At this time, the control unit 300 controls electrical stimulation so that a stronger stimulation than the lowest stimulation is applied to an abdomen of a user. This section can be considered as a section where exercise effect occurs by stimulating upper body fat and muscles in earnest with using an indoor bike.

Looking at time change of an X axis of the graph, it can be seen that as the pedal rotation speed decreases over time, a stimulation level decreases in proportion. Until a user stops pedaling, the control unit 300 reduces an intensity or a frequency of electrical stimulation in proportion to the decrease of a pedal speed.

Looking at a pedal stop section of the graph, even when a user finishes exercise or rests during exercise while not pedaling, the control unit 300 controls the electrical stimulation unit 200 to continue to generate electrical stimulation above the basic stimulation level. The stimulation level may be maintained at the basic stimulation level which was initially preset by the control unit 300, but a user may directly change an intensity of electrical stimulation through the electrical stimulation unit 200.

FIG. 5 only shows a change in pedal speed according to an embodiment of the present invention, so it would be obvious that since various speed changes may occur when a user performs exercise, the control unit 300 can control the electrical stimulation unit 200 to generate electrical stimulation corresponding to various speed changes.

While a user performs a bicycle pedaling exercise, the control unit 300 differently controls electrical stimulation generated at the electrical stimulation unit 200 according to the pedal movement of the stationary bicycle 100. Specifically, a position of the electrical stimulation unit 200 where stimulation generated varies according to the muscles of the leg which a user uses on exercising. When a right pedal of the stationary bicycle 100 is lowered, the control unit 300 controls the electrical stimulation unit 200 to apply a stimulation to an upper body muscles interconnecting to the user's right thigh muscle exercise. Since the control unit 300 may control electrical stimulation so that a current can flow selectively to each electrode pad of the plurality of electrode pads of the electrical stimulation unit 200, a user may perform effective exercises by applying electrical stimulation to upper body muscles through a leg movement.

On the other hand, when a user selects one of programs embedded in the stationary bicycle 100 and performs exercise using the program, the control unit 300 controls electrical stimulation generated at the electrical stimulation unit 200 according to each speed profile defined in multiple programs.

Here, the speed profile refers to a data set of speed changes pre-stored in one program. An intensity and a frequency of electrical stimulation corresponding to each speed profile generated at the electrical stimulation unit 200 is different for each program.

Figure 6:
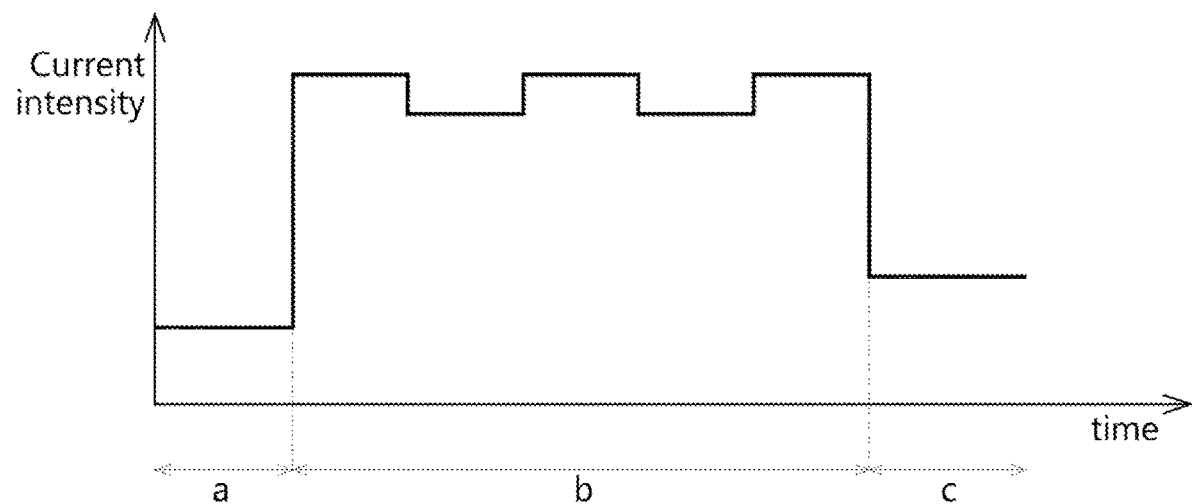
FIG. 6 is a graph showing changes in an electrical stimulation level and a speed profile defined in a program according to an embodiment of the present invention.

FIG. 6 is a graph showing a speed profile and a change in stimulation level defined in a program according to an embodiment of the present invention.

Referring to FIG. 6, the speed profile includes a warm-up step (a), an intensive exercise step (b), and a finishing step (c).

The warm-up step (a) is a low speed step in which a pedal starts rotating and maintains for a predetermined time, and corresponds to a preparation step before a user performs a full-scale exercise.

In the warm-up step (a), weak electrical stimulation is applied to the body to which an electrode pad is attached in response to the rotation of the pedal. The control unit 300 controls the electrical stimulation unit 200 for a weak current to sequentially flow through a plurality of electrode pads, so that a user can feel massage effect through electrical stimulation on portion of the body attached by the pad.

In addition, the heat providing unit provides heat to relax muscles of the body to which the electrode pad is attached in the warm-up step (a), so as to prevent injury by raising body temperature before an intensive exercise.

The intensive exercise step (b) is a step in which a pedal rotates at a relatively high speed, and corresponds to a step in which a user performs a full-scale exercise. In the intensive exercise step (b), electrical stimulation is changed in proportion to a rotation speed of the pedal. A user performs exercise according to a pedal load or rotation speed presented in the selected profile, and the control unit 300 causes the electrical stimulation unit 200 to generate a corresponding electrical stimulation.

If a rotation speed at which a user rotates the pedal is lower than the speed predetermined in a speed profile, the control unit 300 controls the electrical stimulation unit 200 to generate stronger electrical stimulation than electrical stimulation corresponding to the speed profile. Even when a pedal rotation of a user is getting slow, the control unit 300 controls to generate a stronger stimulation so as to maintain exercise effect through electrical stimulation. The control unit 300 may indirectly notify a user to increase the pedal rotation speed by increasing an intensity of stimulation or increasing a frequency of stimulation.

Afterwards, when the user rotates a pedal to fit the predetermined speed, the control unit 300 controls the electrical stimulation unit 200 to generate electrical stimulation corresponding to the preset speed profile again.

Meanwhile, when a user selects a load other than the pedal load preset in the program, the control unit 300 may change an intensity of stimulation of the speed profile in order to correspond to the changed pedal load. Specifically, when a pedal load is lower than the load preset in the program, the control unit 300 may decrease a stimulation, and when a pedal load is higher than the load preset in the program, the control unit 300 may increase a stimulation, based on an intensity of stimulation preset in the program.

The finishing step (c) is a step in which a pedal which rotated at a high speed gradually stops by rotating at a relatively low speed, and corresponds to a step of ending the intensive exercise step and finishing exercise. In the finishing step (c), in order to relax tense muscles by intensive exercise, the control unit 300 controls an intensity or a frequency of stimulation to generate weak electrical stimulation. Like in the warm-up step (a), the control unit 300 may allow a current to sequentially flow through a plurality of electrode pads, so as to help to relax tense muscles and recover fatigue.

FIG. 6 shows only an example of one program among a plurality of programs, and it would be obvious that various speed profiles may be implemented separately.

Figure 7:
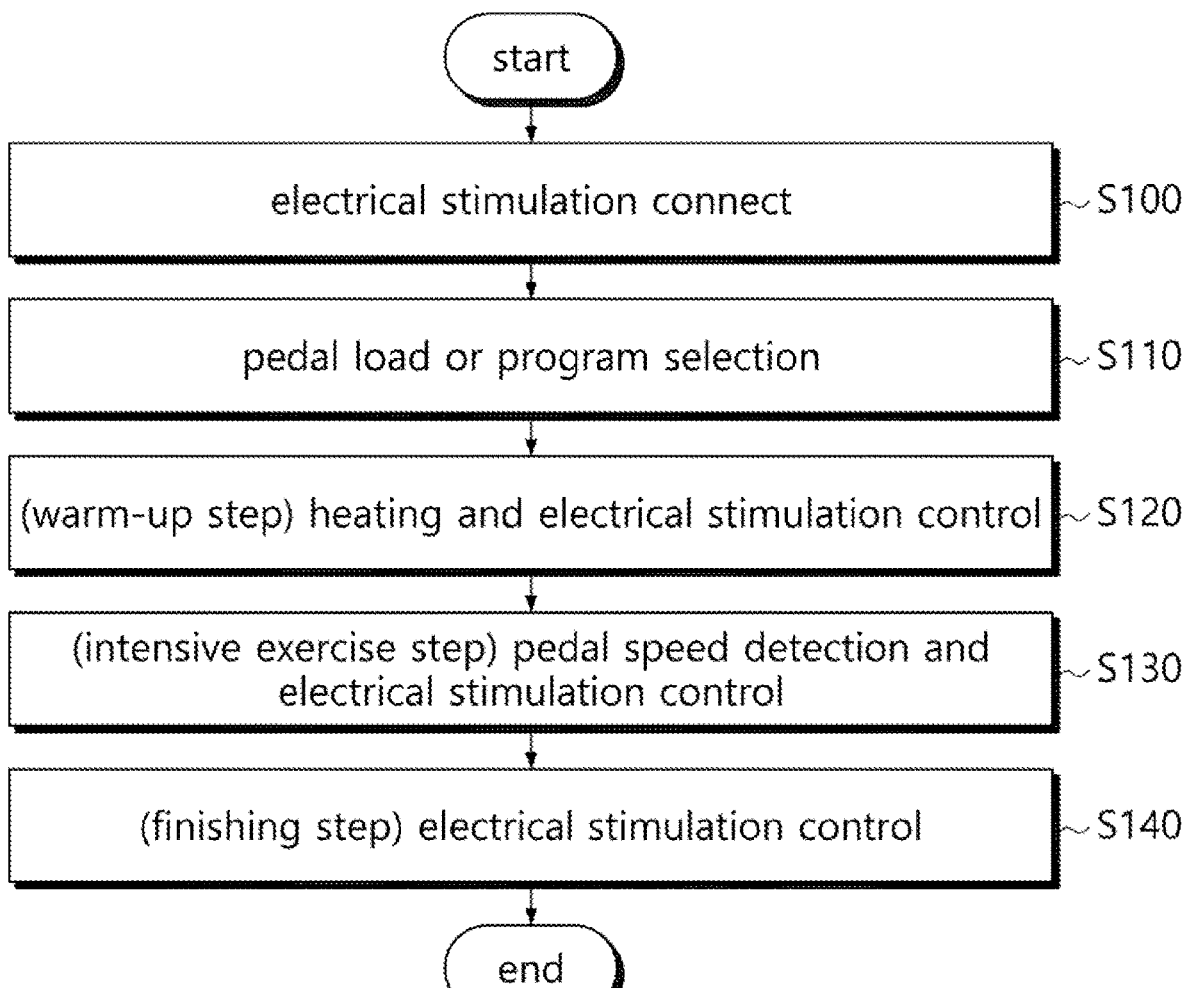
FIG. 7 is a flowchart illustrating an exercise method using an electrical stimulation indoor bike according to an embodiment of the present invention.

FIG. 7 is a flowchart showing an exercise method using an electrical stimulation indoor bike according to an embodiment of the present invention.

First, before starting exercise, a user attaches an electrical stimulation unit 200 on an abdomen or an arm, and connects the electrical stimulation unit 200 to a stationary bicycle 100 with wire or without wire (S100). The user may exercise according to a pedal load preset in the stationary bicycle 100 or may select an exercise mode. The user may select one of a plurality of programs that define a pedal load or speed profile of the stationary bicycle 100, and then start exercising (S110).

When one program is selected, the user performs exercise through a warm-up step, an intensive exercise step, and a finishing step according to the speed profile defined in the program.

In the warm-up step, a heat providing unit provides heat to a portion to which an electrode pad is attached, and the control unit 300 controls the electrical stimulation unit 200 to give a basic stimulation level or to generate electrical stimulation corresponding to the speed profile (S120).

In the intensive exercise step, as a pedal rotation speed increases, electrical stimulation generated at the electrical stimulation unit 200 may increase. The control unit 300 controls to generate electrical stimulation corresponding to the speed profile (S130).

If the user loses concentration while watching TV for a while and does not press a pedal at a speed corresponding to the speed profile, the control unit 300 causes stronger electrical stimulation than electrical stimulation corresponding to the speed profile to be applied for a certain period of time, so that the user can be forced to increase a pedal speed up to the speed corresponding the speed profile.

In the finishing step, as a pedal rotation speed decreases, electrical stimulation generated at the electrical stimulation unit 200 decreases, and the control unit 300 controls a weak electrical stimulation for muscle relaxation to be maintained until a pedal stops rotating (S140).

FIG. 7 is a flowchart of an exercise method using an electrical stimulation indoor bike with selection of an exercise mode according to an embodiment of the present invention. Alternatively, a user may select a program and then adjust a pedal load while exercising, and the control unit 300 may control the electrical stimulation unit 200 variously such that various stimulations corresponding to the adjustment may be generated.

In addition, the control unit 300 controls an intensity or a frequency of electrical stimulation generated at the electrical stimulation unit 200 according to an exercise mode selected by a user. When the user inputs a pedal load, the control unit 300 controls to generate electrical stimulation corresponding to the pedal load.

As described above, according to the present invention, since electrical stimulation corresponding to a bike exercise is applied to a body through the electrical stimulation indoor bike, it is possible to further improve exercise effect simultaneously with effect of losing weight. In addition, since electrical stimulation is applied to correspond to a speed profile of programs embedded in an indoor bike, it is possible to provide an effective muscle exercise effect to the body through various electrical stimulation.

The embodiments of the present invention have been briefly described so far, but it will be understood by those skilled in the art that the embodiments of the present invention can be modified without departing from the technical spirit of the present invention.

Therefore, it should be understood that the protection scope of the present invention extends to the equivalents of the invention described in the claims, and the embodiments of the present invention are illustrative.

The invention claimed is:

1. An electrical stimulation indoor bike comprising:
a stationary bicycle having a pedal;
an electrical stimulation unit connected to the stationary bicycle with wire or wirelessly, and including an electrode pad for applying electrical stimulation to a user's body; and
a control unit configured to control electrical stimulation of the electrical stimulation unit in accordance with an exercise mode of the stationary bicycle,
wherein the exercise mode includes a plurality of programs that define a pedal load and/or a speed profile of the stationary bicycle to be selected by a user's input,
wherein the control unit is configured to change an intensity or a frequency of electrical stimulation generated at the electrical stimulation unit in accordance with the pedal load and/or the speed profile, and
wherein, when one of the plurality of programs is selected and a pedal load other than a pedal load preset in the selected program is selected, an intensity of electrical stimulation corresponding to the speed profile is changed depending on the selected pedal load.

2. The electrical stimulation indoor bike of claim 1, wherein,
when a pedal load of the stationary bicycle is input by a user or predetermined,
the control unit provides a basic stimulation level corresponding to the pedal load, and controls electrical stimulation of the electrical stimulation unit so as to generate stronger stimulation than the basic stimulation level in proportion to a rotation speed of the pedal.

3. The electrical stimulation indoor bike of claim 1, wherein
the control unit controls the electrical stimulation unit so as to generate stronger electrical stimulation than electrical stimulation corresponding to the speed profile, when a rotation speed of the pedal is slower than that defined in the speed profile.

4. An electrical stimulation indoor bike comprising:
a stationary bicycle having a pedal;
an electrical stimulation unit connected to the stationary bicycle with wire or wirelessly for applying electrical stimulation to a user's body; and
a control unit configured to control electrical stimulation of the electrical stimulation unit in accordance with an exercise mode of the stationary bicycle,
wherein the electrical stimulation unit includes a plurality of electrode pads,
wherein the control unit controls electrical stimulation of the electrical stimulation unit so that a current selectively flows to each electrode pad of the plurality of electrode pads, and
wherein the control unit controls electrical stimulation of the electrical stimulation unit so that a current flows to an electrode pad attached to user's upper body muscles which respond in accordance with lowering of the pedal, when the user lowers the pedal of the stationary bicycle.

5. An electrical stimulation indoor bike comprising:
a stationary bicycle having a pedal;
an electrical stimulation unit connected to the stationary bicycle with wire or wirelessly, and including an electrode pad for applying electrical stimulation to a user's body; and
a control unit configured to control electrical stimulation of the electrical stimulation unit in accordance with an exercise mode of the stationary bicycle,
wherein the exercise mode includes a plurality of programs that define a pedal load or a speed profile of the stationary bicycle selected by a user's input,
wherein the control unit is configured to change an intensity or a frequency of electrical stimulation generated at the electrical stimulation unit in accordance with the pedal load or the speed profile,
wherein the speed profile comprises:
a warm-up step in which the pedal starts rotating and increases a rotation speed up to a predetermined speed at a low speed,
an intensive exercise step in which the pedal rotates from the predetermined speed to a higher speed, and
a finishing step in which the pedal rotates from the speed of the intensive exercise step to a lower speed to be stopped,
wherein the control unit controls the electrical stimulation unit so as to generate electrical stimulation corresponding to each step,
wherein the electrical stimulation unit includes a heat providing unit for providing heat to a user's body area to which the electrode pad is attached, and
wherein the heat providing unit is configured to relax muscles of the user's body area to which the electrode pad is attached at the warm-up step.

* * * * *